United States Patent
Ahn

(10) Patent No.: US 7,471,076 B2
(45) Date of Patent: Dec. 30, 2008

(54) APPARATUS FOR MEASURING NUMBERS OF PARTICLES AND METHOD THEREOF

(75) Inventor: Kang-Ho Ahn, 102-1504 Ichon Apt., Ichon-dong, Yongsan-gu, Seoul (KR) 140-030

(73) Assignees: Hyundai Calibration & Certification Technologies Co., Ltd., Echun-Si, Gyeonggi-Do (KR); Kang-Ho Ahn, Seoul (KR)

( * ) Notice: Subject to any disclaimer, the term of this patent is extended or adjusted under 35 U.S.C. 154(b) by 0 days.

(21) Appl. No.: 10/597,934

(22) PCT Filed: Feb. 14, 2005

(86) PCT No.: PCT/KR2005/000401

§ 371 (c)(1),
(2), (4) Date: Aug. 11, 2006

(87) PCT Pub. No.: WO2005/078409

PCT Pub. Date: Aug. 25, 2005

(65) Prior Publication Data

US 2007/0194775 A1 Aug. 23, 2007

(30) Foreign Application Priority Data

Feb. 13, 2004 (KR) ...................... 10-2004-0009492

(51) Int. Cl.
*G01N 27/00* (2006.01)
*G01N 15/00* (2006.01)
(52) U.S. Cl. ..................................... 324/71.4; 73/865.5
(58) Field of Classification Search .............. 324/71.4; 73/865.5

See application file for complete search history.

(56) References Cited

U.S. PATENT DOCUMENTS

| 5,056,355 | A |   | 10/1991 | Hepher et al. |
|-----------|---|---|---------|---------------|
| 5,489,506 | A | * | 2/1996  | Crane ........................ 324/71.4 |
| 5,922,976 | A |   | 7/1999  | Russell et al. |
| 6,230,572 | B1 |  | 5/2001  | Pui et al. |
| 6,263,744 | B1 |  | 7/2001  | Russell et al. |
| 6,281,972 | B1 | * | 8/2001 | Ebara et al. .................. 356/336 |
| 6,639,671 | B1 | * | 10/2003 | Liu ........................... 73/28.01 |
| 6,905,029 | B2 | * | 6/2005 | Flagan ........................ 209/210 |
| 7,145,320 | B2 | * | 12/2006 | Yoshida et al. ............. 324/71.4 |

* cited by examiner

*Primary Examiner*—Timothy J Dole
(74) *Attorney, Agent, or Firm*—Lowe Hauptman Ham & Berner

(57) ABSTRACT

The present invention discloses apparatus and method for rapidly and easily measuring the numbers and size distribution of low concentration particles which exist in a clean space such as a clean room. The apparatus and method according to the present invention measures the numbers of particles by charging particles to a monopolarity, collecting the particles by applying a voltage to an electrode and attaching the charged particles of a certain size or less thereto, separating the charged particles of the certain size or more according to size by the particle separating ducts. The apparatus for measuring the number of particles according to the present invention makes it possible to obtain a size distribution of particles in the air by a single measurement and to rapidly and easily measure it even though the number of the particles in the air is small.

5 Claims, 6 Drawing Sheets

APPARATUS FOR MEASURING NUMBERS OF PARTICLES AND METHOD THEREOF

RELATED APPLICATIONS

The present application is a National Phase application based on International Application Number PCT/KR2005/000401, filed Feb. 14, 2005, which claims priority from, Korean Application Number 10-2004-0009492, filed Feb. 13, 2004, the disclosure of which is hereby incorporated by reference herein in its entirety.

TECHNICAL FIELD

The present invention relates to an apparatus and method for measuring the numbers of particles, and more particularly, to an apparatus and method for easily and rapidly measuring the numbers and a size distribution of low concentration particles existing in a clean space such as a clean room.

BACKGROUND ART

As is generally known, measurement of the number of particles existing in a clean space such as a clean room is a very important factor in semiconductor production processes. As a prior art, there have been used optical particle counters (OPCs) using a laser, diffusion batteries using Brownian diffusion, or the like in order to measure the size of particles.

As the line widths of semiconductors decrease due to the development of semiconductor technology, particles of about 10 nm in diameter should necessarily be measured. However, the aforementioned optical particle counters cannot measure particles of 0.1 μm or less in diameter due to laser scattering. In addition, when particles are measured using diffusion batteries, there is a problem in that the measurement results are imprecise.

At present, in order to measure particles' of about 10 nm in diameter, differential mobility particle counters have been developed. A differential mobility particle counter comprises a combination of a differential mobility analyzer (DMA) and a condensation particle counter. The differential mobility analyzer selects particles with desired diameters using a particle diameter, particle flow and electrostatic force, and then the condensation particle counter measures the number of particles selected by the differential mobility analyzer using a computer.

FIG. 1 is a view showing an apparatus for measuring the number of particles using the prior art. Referring to FIG. 1, the apparatus for measuring the number of particles of the prior art comprises a particle injector 10, a particle separator 20, and a particle counter 30.

The particle injector 10 is positioned upstream of the particle separator 20. The particle injector 10 includes a particle feeder 12, a neutralizer 14 as a particle charger for charging supplied particles, and a clean air feeder 16. The neutralizer 14 electrically neutralizes particles by charging them to a positive polarity using radioactivity. Since such a neutralizer is well known those skilled in the art to which the present invention pertains, the configuration and operation thereof will be omitted.

The particle separator 20 includes a cylindrical outer guide duct 21, a cylindrical inner guide duct 22, an electrode 23 installed in the inner guide duct 22, and a particle separating duct 24 extending from a lower end of the electrode 23. The electrode 23 is connected to a power supply 25, while the outer the guide duct 21 is grounded. The particle separating duct 24 is formed with a plurality of particle admission holes 24a along an outer peripheral surface of the particle separating duct 24. The particle admission holes 24a are positioned at the same height and each of them is about 1 mm in diameter.

The operation of the apparatus for measuring the number of particles of the prior art so configured will be described. When particles are fed from the particle feeder 12, the particles are charged to a positive polarity by the neutralizer 14. The charged particles are introduced between the outer guide duct 21 and the inner guide duct 22. In the meantime, in order to smoothly deliver the charged particles to the inner guide duct 22, clean air is introduced into the inner guide duct 22. The particles charged into a polarity opposite to that of the electrode 23 move toward the electrode. Accordingly, charged particles of small size become attached to an upper portion of the electrode 23, and charged particles of large size move to a lower portion of the electrode 23. The charged particles moving downward are attached onto the lower portion of the electrode 23 or the charged particles of very large size, which are not attached onto the electrode 23, flow out of the guide duct 21. At this time, if some air is forcibly sucked through the particle separating duct 24, the particles of a predetermined size that reach the lower portion of the electrode 23 are introduced into the particle separating duct 24 through the particle admission holes 24a by the aforementioned operation of the air suction and then flow out. The charged particles flowing out by the particle separating duct 24 are within a predetermined size range. The selected charged particles are introduced into the particle counter 30 positioned downstream of the particle separator 20, and then, the number of the particles is measured.

Thus, by controlling a voltage applied to the electrode 23, the charged particles can be sorted according to size. If the above process is repeated with the voltage applied to the electrode 23 so controlled, it is possible to measure the number of particles according to size and then to obtain a size distribution of the whole particles.

However, the apparatus for measuring the number of particles of the prior art can only measure the number of the charged particles only within a specified size range by a single measurement. Thus, in order to obtain the numbers and the size distribution of whole particles, there is a disadvantage in that the measurement should be repeated a number of times with differing voltage applied to the electrode. Furthermore, when the particles in the air existing in a clean space such as a clean room are measured, the number of the particles in the clean space is fundamentally small. Thus, in practice, it is impossible to measure the numbers of charged particles according to size by changing voltage.

DISCLOSURE

Technical Problem

Accordingly, the present invention is conceived to solve the aforementioned problems in the prior art. An object of the present invention is to provide an apparatus and method for rapidly measuring the numbers and a size distribution of particles contained in the air at one time.

Another object of the present invention is to provide an apparatus and method for easily measuring the numbers and size distribution of particles even though the number of the particles contained in the air is small.

Technical Solution

According to a first aspect of the present invention for achieving the above objects, there is provided an apparatus for measuring the numbers of particles comprising: a particle charging means for charging particles to a monopolarity; an inner guide duct into which clean air is introduced; an electrode to which a high voltage is applied and which is installed in the inner guide duct in a lengthwise direction of the inner guide duct; a power supplying means for supplying power to the electrode; an outer guide duct positioned outside the inner guide duct and being longer than the inner guide duct, wherein the particles charged by the particle charging means are introduced between the inner guide duct and the outer guide duct; a particle separating means having an upper end positioned at an inner lower side of the outer guide duct and separating the charged particles according to size; and a particle counting means connected to the particle separating means and counting the particles separated according to size by the particle separating means.

According to a second aspect of the present invention, there is provided an apparatus for measuring the numbers of particles comprising: a particle charging means for charging particles; a plurality of particle separators, each of which comprises an inner guide duct into which clean air is introduced, an electrode installed in the inner guide duct in a lengthwise direction of the inner guide duct, and an outer guide duct positioned outside the inner guide duct, being longer than the inner guide duct and including a particle collecting portion downstream of the outer guide duct, wherein the particles charged by the particle charging means are introduced between the inner guide duct and the outer guide duct; a power supplying means for supplying mutually different powers to the respective electrodes of the a plurality of the particle separators so that voltage differences are formed between the respective electrodes; and a plurality of particle counting means measuring particles collected by the respective particle separators.

According to a third aspect of the present invention, there is provided a method for measuring the numbers of particles comprising steps of: charging particles to be measured to a monopolarity; introducing the charged particles and clean air into a guide duct; applying a voltage to an electrode installed in the guide duct; attaching the charged particles of a certain size or less to the electrode; separating the charged particles, which are not attached to the electrode, according to size; and measuring the numbers of the charged particles separated according to size.

According to a fourth aspect of the present invention, there is provided a method for measuring the numbers of particles comprising: preparing a plurality of particle separators, each of which includes a guide duct and an electrode provided in the guide duct; charging particles to be measured to a monopolarity; introducing the charged particles and clean air into the guide ducts; applying mutually different voltages to the electrodes; measuring the numbers of the charged particles separated by the particle separators; and calculating a size distribution of the particles based on the measured results.

BEST MODE

Hereinafter, embodiments of an apparatus for measuring the numbers of particles according to the present invention will be described in detail with reference to the accompanying drawings.

Figure 2:
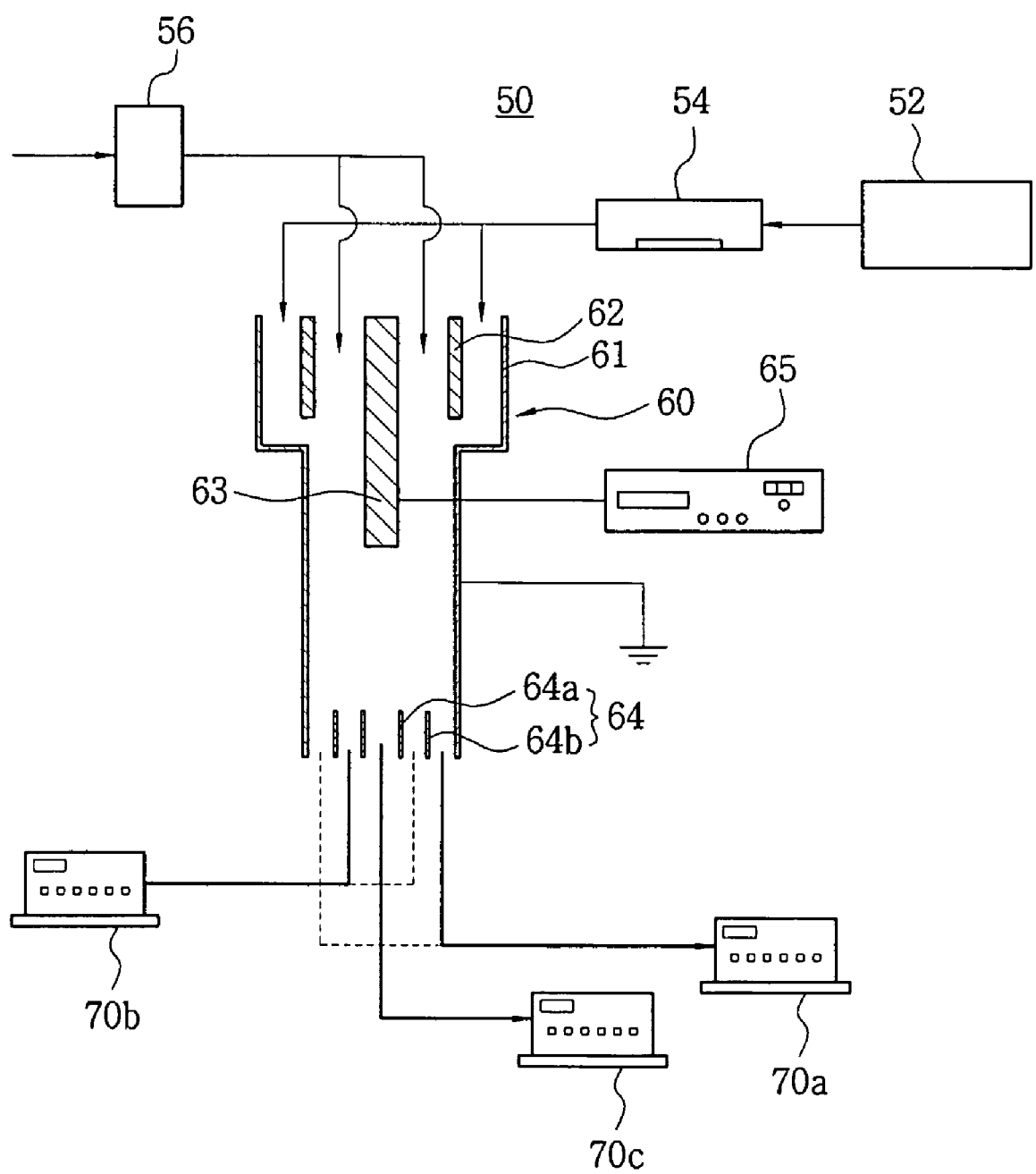
FIG. 2 is a view showing a configuration of a first embodiment of an apparatus for measuring the numbers of particles according to the present invention.

FIG. 2 is a view showing of a first embodiment of the apparatus for measuring the number of particles according to the present invention. As shown in the figure, the apparatus for measuring the number of particles according to the present embodiment comprises a particle injector 50, a particle separator 60, and particle counters 70.

Figure 1:
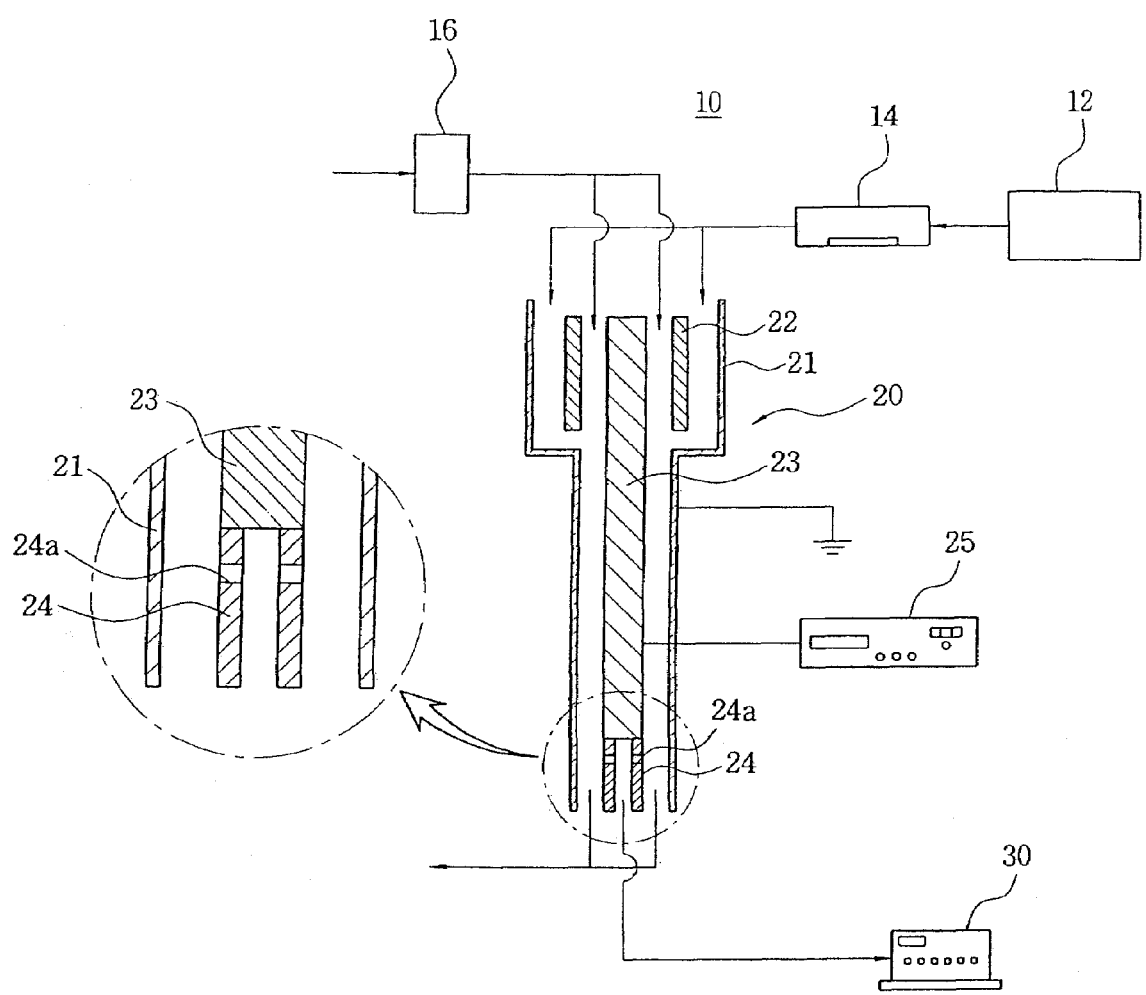
FIG. 1 is a view showing a configuration of an apparatus for measuring the number of particles according to a prior art.

The particle injector 50 is positioned upstream of the particle separator 60. The particle injector 50 includes a particle feeder 52, a particle charger 54 for charging fed particles, and a clean air feeder 56. In contrast with the neutralizer 14 which is the aforementioned particle charger shown in FIG. 1 for charging particles to a positive polarity, the particle charger 54 as a characteristic of the present invention charges the introduced particles to a monopolarity. Such a particle charger 54 charges particles using corona discharge, radioactivity, X-RAY, ultraviolet, or the like. Since the particle charger for charging particles to a monopolarity is well known to those skilled in the art, the detail thereof will be omitted herein.

The particles charged to a monopolarity by the particle charger 54 are introduced into the particle separator 60, and then, the particle separator 60 separates the particles according to size. The particle separator 60 includes a cylindrical outer guide duct 61, a cylindrical inner guide duct 62, an electrode 63 installed in the inner guide duct 62, a plurality of particle separating ducts 64 (64a and 64b) that are installed at a inner lower side of the outer guide duct 61 concentrically with the outer guide duct 61 and separate particles according to size. According to the present embodiment, the particles are separated and sorted according to size. The electrode 63 is connected to a power supply 65, and the outer guide duct 61 is grounded. The electrode 63 is spaced apart by a predetermined distance, for example, about 1 to 5 cm, from an upper end of the particle separating ducts 64a and 64b in order for the particles to be separated according to size and flow out. As described above, the particle separator 60 according to the present embodiment differs from the particle separator 20 of the prior art shown in FIG. 1, that is, the shape and the number of the particle separating ducts 64 differ from those of the particle separating duct 24, and the gap between the electrode 63 and the particle separating ducts 64 also differs from that between the electrode 23 and the particle separating duct 24.

The particle counters 70a, 70b, and 70c are positioned downstream of the particle separator 60. The particle counters are installed according to size of the particles to be measured. Since the particle counter is well known, detail thereof will be omitted.

The operation of the first embodiment of the apparatus for measuring the numbers of particles according to the present invention so configured will be described.

Figure 3:
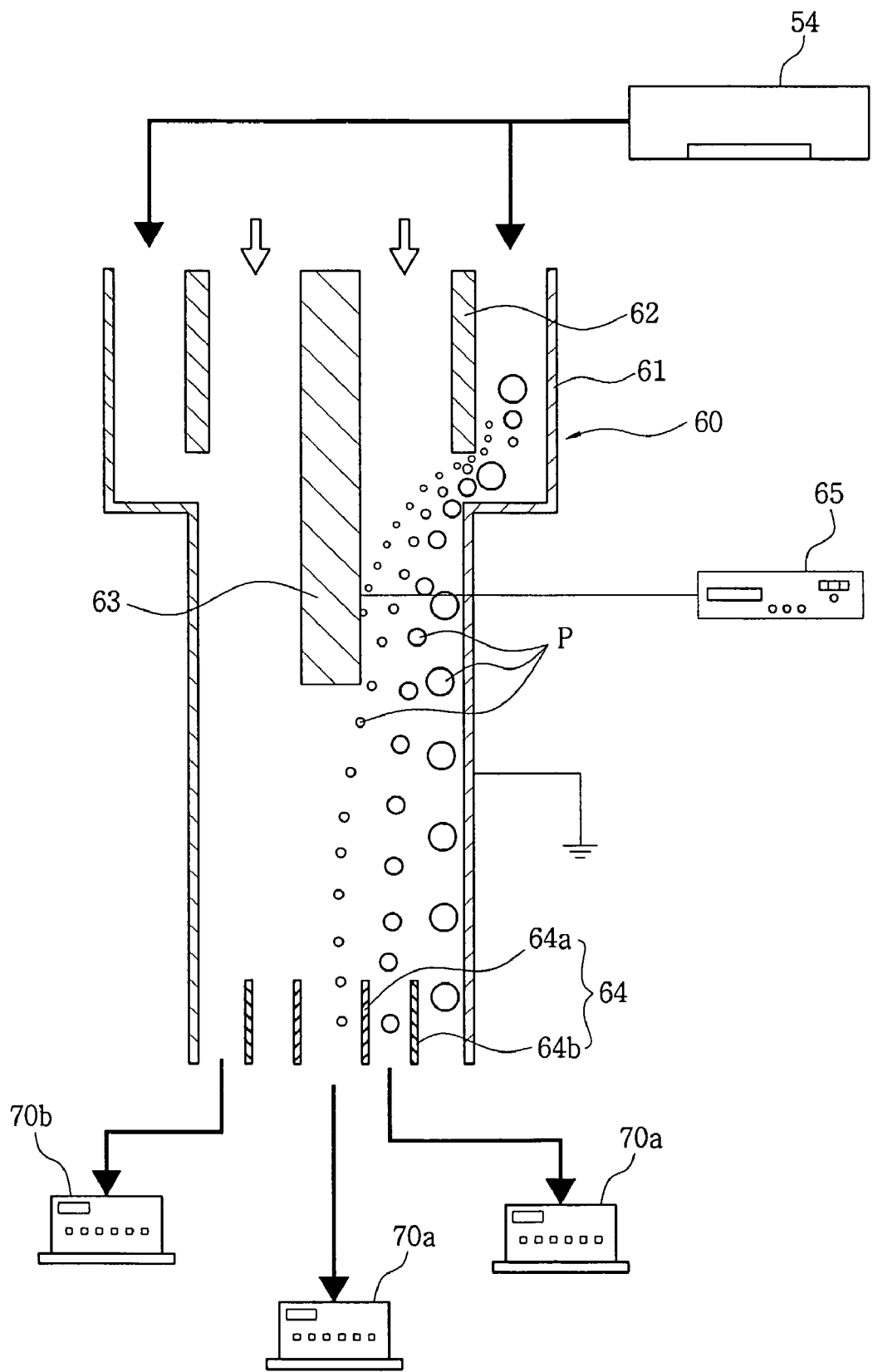
FIG. 3 is an enlarged sectional view illustrating motion of charged particles in a particle separator according to FIG. 2.

Referring to FIG. 3, the particles fed through the particle feeder 52 are charged to a monopolarity by the particle charger 54, and the charged particles are introduced into the particle separator 60. The charged particles P are introduced between the outer guide duct 61 and the inner guide duct 62, and then, the introduced charged particles P move and descend along mutually different traces according to particle size. When a high voltage with a polarity opposite to that of the charged particles P is applied to the electrode 63, the charged particles P move toward the electrode 63 by electrostatic force. Thus, assuming that electric charge quantity of a particle is constant independent of size of the particles, (particles of 100 nm or less generally have an electric charge) the moving velocity of particles can be expected to be a function of particle size and the applied voltage.

Referring to FIG. 3, when a constant voltage is applied to the electrode 63, particles of small size become attached to and collected on the electrode 63, and particles of large size are not collected on the electrode 63 and flow out of the particle separator 60. Among the charged particles P not collected on the electrode 63, particles of the largest size move between the outer guide duct 61 and the particle separating duct 64b farthest from the centerline of the electrode 63 and are separated, particles of middle size move between the particle separating duct 64a and the particle separating duct 64b and are separated, and charged particles of the smallest size move into the particle separating duct 64a closest from the centerline of the electrode 63 and are separated.

Accordingly, the respective particle counters 70a, 70b and 70c positioned downstream of the outer guide duct 61 measure the numbers of the charged particles P separated according to size. The numbers of the charged particles P are measured by the particle counters 70a, 70b and 70c, so that it is possible to obtain a size distribution of particles in the air existing in the clean space.

Next, a second embodiment of the apparatus for measuring the numbers of particles according to the present invention will be described.

Figure 4:
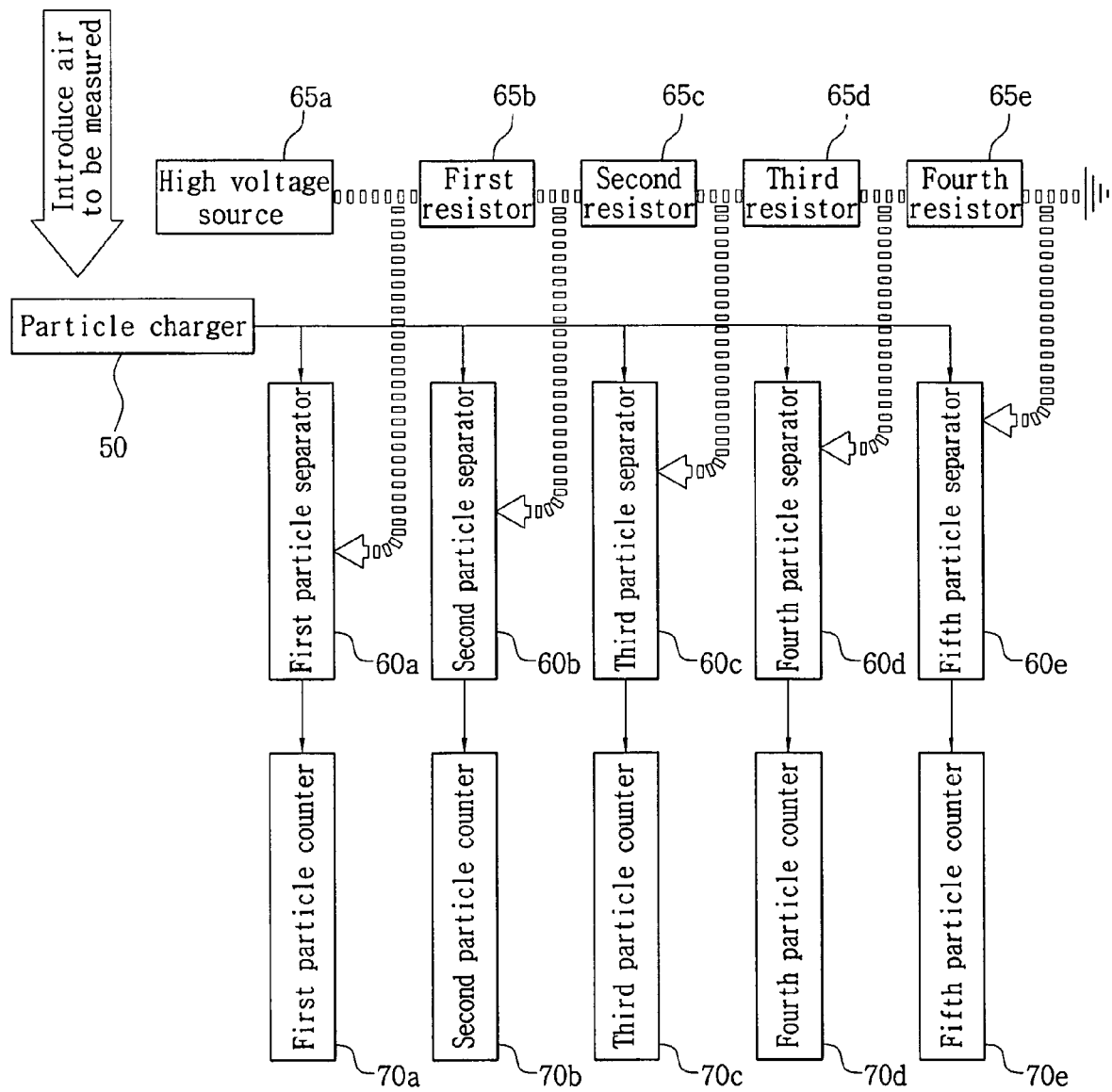
FIG. 4 is a view showing a configuration of a second embodiment of the apparatus for measuring the numbers of particles according to the present invention.

FIG. 4 is a view showing the second embodiment of the present invention. The apparatus for measuring the numbers of particles according to the present embodiment includes a particle charger 50, a plurality of particle separators 60a to 60e, a power supply 65a to 65e applying voltages to electrodes of the respective particle separators 60a to 60e, a plurality of particle counters 70a to 70e connected and installed corresponding to the respective particle separators 60a to 60e.

Each of the particle separators 60a to 60e is the same as the particle separator 60 of FIG. 2 in the fundamental configuration. However, each of the particle separators 60a to 60e of the present embodiment does not include a plurality of the particle separating ducts 64a and 64b unlike the particle separator 60 of FIG. 2 and the outer guide duct 61 itself functions as the particle separating duct. A lower portion of the outer guide duct has a funnel shape with a gradually narrowing inlet, and particles directly flow out to the particle counter in communication with the outer guide duct.

The power supply 65a to 65e consists of a high voltage source 65a and a plurality of resistors 65b to 65e serially connected to the high voltage source 65a. Voltages dropped by the resistors 65b to 65e are applied to the electrodes of the respective particle separators 60b to 60e, and a zero voltage is applied to the electrode of the last particle separator 60e.

In the present embodiment, the particle separators 60a to 60e and the particle counters 70a to 70e are installed in parallel. The mutually different voltages are applied to the respective electrodes of the particle separators 60a to 60e, so that the first particle separator 60a separates only particles of largest size and causes them to flow out, and the second particle separator 60b separates particles of the second largest size or more and causes them to flow out. Furthermore, the third and fourth particle separators 60c and 60d separate particles of smaller sizes or more and cause them to flow out. Finally, since zero voltage is applied to the electrode of the fifth particle separator 60e, particles of all sizes flow out through the fifth particle separator 60e. As described above, each of the particle separators 60a to 60e and each of the particle counters 70a to 70e measure the number of particles of a specific size or more according to the analyzer and counter. Thus, by analyzing the collected data after connecting a computer to the apparatus for measuring the numbers of particles of the present embodiment, it is possible to measure the size distribution of particles existing in a clean space.

Figure 5:
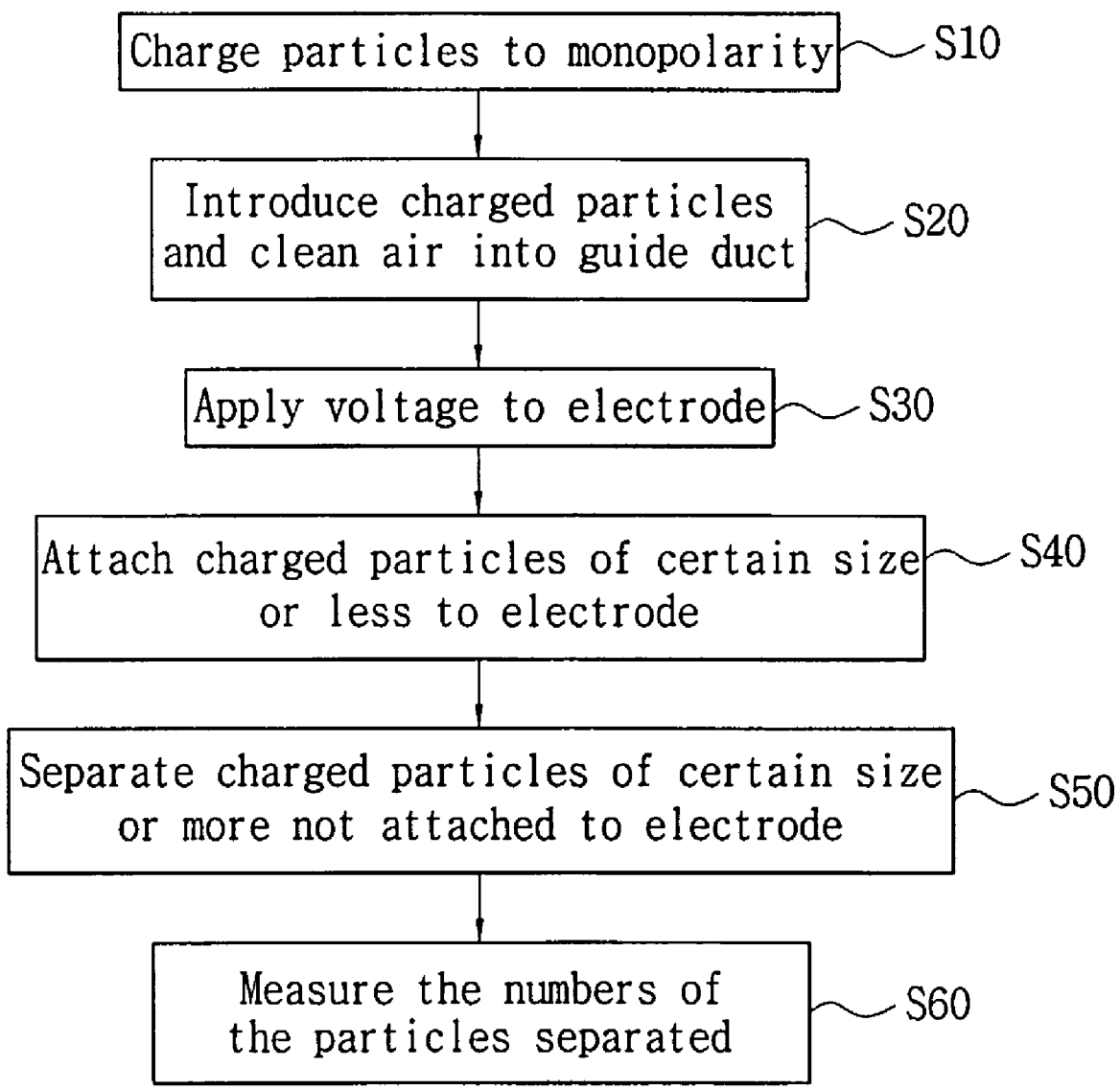
FIG. 5 is a flowchart illustrating a first embodiment of a method for measuring the numbers of particles according to the present invention.

Hereinafter, a first embodiment of a method for measuring the numbers of particles according to the present invention will be described with reference to FIG. 5.

In order to measure the numbers of particles, the particles to be measured are charged to a monopolarity (step S10). The process of charging the particles to a monopolarity is performed by the particle charger described above. Then, the charged particles and clean air are introduced into a guide duct (step S20). The guide duct includes an inner guide duct and an outer guide duct that is positioned outside the inner guide duct and is longer than the inner guide duct. The charged particles are introduced between the outer guide duct and the inner guide duct, while the clean air is introduced into the inner guide duct.

Thereafter, a voltage is applied to an electrode installed in the inner guide duct (step S30). The electrode is installed in the lengthwise direction of the guide duct, longer than the inner guide duct and shorter than the outer guide duct. The charged particles of a certain size or less out of the charged particles introduced into the guide duct become attached to the electrode by the voltage applied to the electrode (step S40). The size of the charged particles attached may be controlled by controlling the voltage applied to the electrode.

Then, the charged particles of the certain size or more that do not become attached to the electrode are separated according to size (step S50). In order to sort the particles, as in the first embodiment of the apparatus for measuring the numbers of particles described above, a plurality of particle separating ducts are installed at a lower end of the outer guide duct. The particle separating ducts are concentrically installed. Since the charged particles descend in the guide duct along mutually different traces according to size, the charged particles move to the particle separating ducts installed at the lower end of the guide duct and then are separated. The particles separated by the particle separating ducts are separated according to size. The numbers of particles separated by the particle separating ducts are measured (step S60), thus obtaining the size distribution of the particles.

Figure 6:
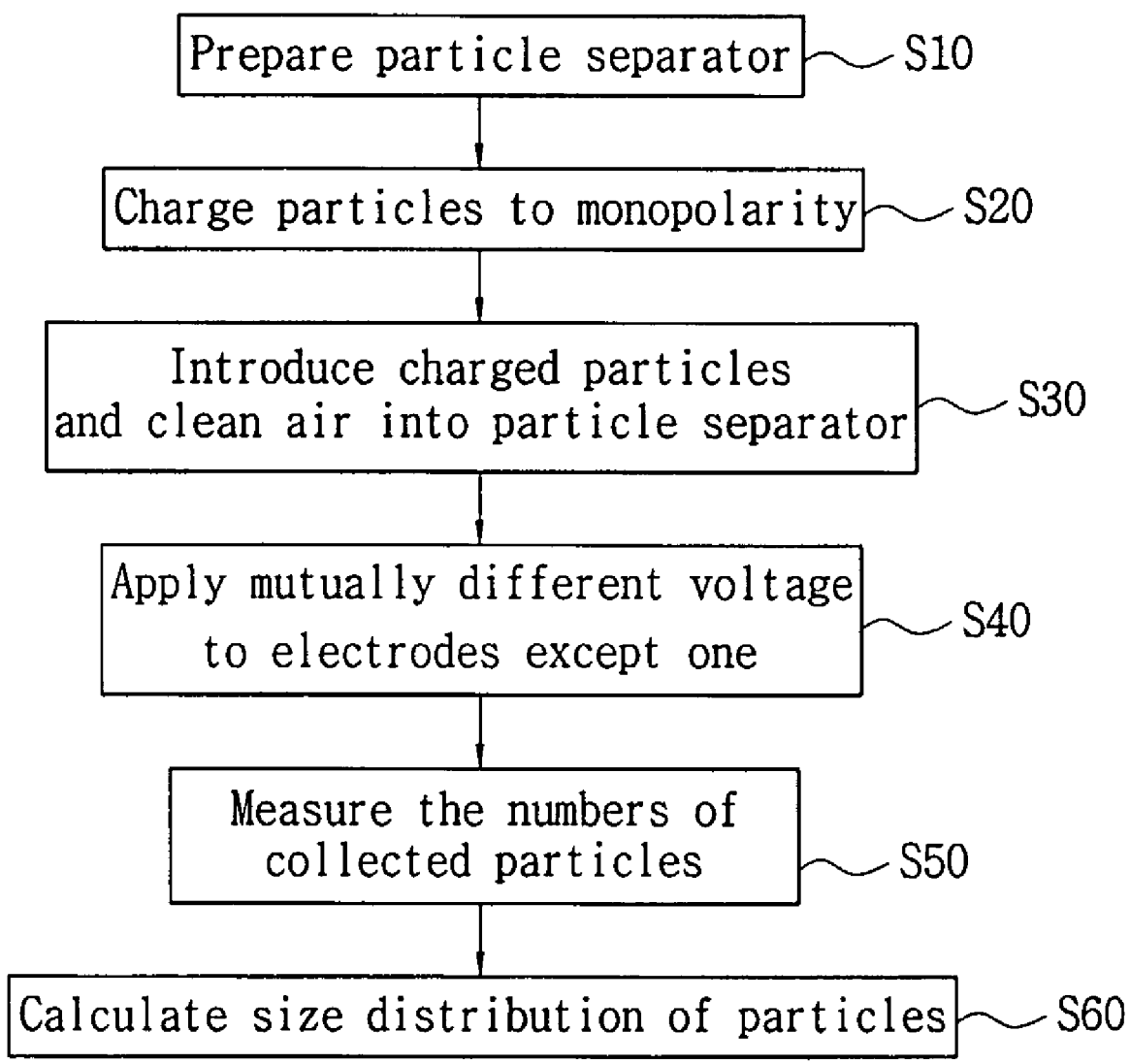
FIG. 6 is a flowchart illustrating a second embodiment of the method for measuring the numbers of particles according to the present invention.

Next, a second embodiment of the method for measuring the numbers of particles according to the present invention will be described with reference to FIG. 6.

In the second embodiment of the method for measuring the numbers of particles, a plurality of particle separators are prepared, each of which is provided with a guide duct and an electrode installed in the lengthwise direction of the guide duct (step S10). The guide duct includes an inner guide duct and an outer guide duct that is positioned outside the inner guide duct and is longer than the inner guide duct. Then, particles to be measured are charged to a monopolarity (step S20). The charged particles are introduced between the outer guide duct and the inner guide duct, while the clean air is introduced into the inner guide duct (step S30).

Next, mutually different voltages are applied to the electrodes of the respective particle separators (step S40). While zero voltage is applied to one of the electrodes, stepwise decreasing voltages are applied to the other respective electrodes. The mutually different voltages are applied to the electrodes of the respective particle separators, so that the particle separator including the electrode to which a high voltage is applied causes only particles of the largest size to be separated and flow out, and the other particle separators to which the stepwise decreasing voltages are applied cause particles of stepwise decreasing sizes or more to be separated and flow out, respectively. Through the particle separator to which the zero voltage is applied, particles of all sizes flow out.

When the charged particles flow out through the respective particle separators, the number of particles of a specific size or more can be measured in each of the particle separators through a step S50 for measuring the numbers of the separated charged particles. Finally, a size distribution of the particles is calculated based on the measured results (step S60). If the data measured from the respective particle separators are analyzed using a computer in step S60, the size distribution of the particles existing in the clean space can be measured. That is, when the number of the particles separated by the particle separator to which a high voltage is applied is subtracted from the number of the particles separated by the particle separator to which a lower voltage is applied, it is possible to calculate the number of the particles of a specified size range. Thus, according to the method for measuring the number of particles of the present invention, it is possible to rapidly measure the size distribution of the particles.

The embodiments described above are only examples of the apparatus and method for measuring the numbers of particles of the present invention. The scope of the present invention is not limited to the embodiments described above. It will be apparent that those skilled in the art can make various modifications, changes, and substitutions within the technical spirit of the invention and the scope defined by the claims. It is understood that such embodiments pertain to the scope of the present invention.

INDUSTRIAL APPLICABILITY

As described above, the apparatus and method for measuring the number of particles according to the present invention makes it possible to obtain a size distribution of particles in the air by a single measurement. In addition, the apparatus and method for measuring the number of particles according to the present invention makes it possible to easily obtain the size distribution of particles in the air even though the number of the particles contained in the air is small.

The invention claimed is:

1. An apparatus for measuring a number of particles comprising:
    a particle charging means for charging particles to a monopolarity;
    an inner guide duct into which clean air is introduced;
    an electrode to which a high voltage is applied, the electrode being installed in the inner guide duct in a lengthwise direction of the inner guide duct;
    a power supplying means for supplying power to the electrode;
    an outer guide duct positioned outside the inner guide duct and being longer than the inner guide duct, the particles charged by the particle charging means being introduced between the inner guide duct and the outer guide duct;
    a particle separating means having an upper end positioned at an inner lower side of the outer guide duct and including a plurality of particle separating ducts that are spaced apart from a lower end of the electrode, wherein an empty space is formed between the lower end of the electrode and an upper end of the particle separating ducts and the particle separating means separates the charged particles according to size when the charged particles flow down in the empty space; and
    a particle counting means connected to the particle separating means for counting the particles separated according to size by the particle separating means.

2. The apparatus as claimed in claim 1, wherein the particle counting means includes a plurality of particle counters connected to the respective particle separating ducts.

3. The apparatus as claimed in claim 2, wherein the particle separating ducts are concentrically installed.

4. A method for measuring a number of particles comprising steps of:
    charging particles to be measured to a monopolarity;
    introducing the charged particles and clean air into a guide duct;
    applying a voltage to an electrode installed in the guide duct;
    attaching the charged particles of a certain size or less to the electrode;
    separating the charged particles, which are not attached to the electrode, according to size into a plurality of groups; and
    counting the number of charged particles of each group separated according to size.

5. The method as claimed in claim 4, wherein the size of the charged particles attached to the electrode is controlled by changing the voltage applied to the electrode.

* * * * *